US012673127B2

(12) United States Patent
Yuki et al.

(10) Patent No.: US 12,673,127 B2
(45) Date of Patent: Jul. 7, 2026

(54) LIQUID EMBOLIC MATERIAL COMPOSITION

(71) Applicant: THE REGENTS OF THE UNIVERSITY OF CALIFORNIA, Oakland, CA (US)

(72) Inventors: Ichiro Yuki, Irvine, CA (US); Shuichi Suzuki, Irvine, CA (US); Kousaku Ohkawa, Irvine, CA (US); Frank P.K. Hsu, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 975 days.

(21) Appl. No.: 17/756,234

(22) PCT Filed: Nov. 20, 2020

(86) PCT No.: PCT/US2020/061472
§ 371 (c)(1),
(2) Date: May 19, 2022

(87) PCT Pub. No.: WO2021/102241
PCT Pub. Date: May 27, 2021

(65) Prior Publication Data
US 2023/0001043 A1     Jan. 5, 2023

Related U.S. Application Data

(60) Provisional application No. 62/938,110, filed on Nov. 20, 2019.

(51) Int. Cl.
| | |
|---|---|
| *A61L 24/00* | (2006.01) |
| *A61L 24/04* | (2006.01) |
| *A61L 24/08* | (2006.01) |

(52) U.S. Cl.
CPC ........... *A61L 24/001* (2013.01); *A61L 24/043* (2013.01); *A61L 24/08* (2013.01); *A61L 2300/214* (2013.01); *A61L 2300/232* (2013.01); *A61L 2400/06* (2013.01); *A61L 2430/36* (2013.01)

(58) Field of Classification Search
CPC ......... A61L 2300/214; A61L 2300/232; A61L 24/001; A61L 24/043; A61L 24/08; A61L 2400/06; A61L 2430/36; A61K 49/0457
See application file for complete search history.

(56) References Cited

U.S. PATENT DOCUMENTS

| | | | |
|---|---|---|---|
| 5,667,767 | A | 9/1997 | Greff et al. |
| 5,695,480 | A | 12/1997 | Evans et al. |
| 5,830,178 | A | 11/1998 | Jones et al. |
| 2006/0069168 | A1 | 3/2006 | Tabata et al. |
| 2013/0108574 | A1 | 5/2013 | Chevalier et al. |
| 2014/0274945 | A1 | 9/2014 | Blaskovich et al. |
| 2015/0018872 | A1 | 1/2015 | Wilkie |
| 2016/0089454 | A1* | 3/2016 | Andresen ........... A61K 49/1806 |
| | | | 424/9.4 |
| 2016/0129220 | A1 | 5/2016 | Jagadeesan et al. |
| 2020/0009290 | A1* | 1/2020 | Yuki ........................ A61L 24/02 |

FOREIGN PATENT DOCUMENTS

| | | |
|---|---|---|
| CN | 103126973 B | 2/2015 |
| WO | WO2019163012 A1 | 8/2019 |

OTHER PUBLICATIONS

Hsu, Ming Fang, et al. Hyaluronic acid-based nano-sized drug carrier-containing Gellan gum microspheres as potential multifunctional embolic agent. Sci Rep 8, 731 (2018). https://doi.org/10.1038/s41598-018-19191-7.
International Search Report for PCT/US20/61472 (WO2021102241 Published May 27, 2021).
Morris, Edwin R. et al., Gelation of gellan—A review. Food Hydrocolloids. 28. 373-411. 10.1016/j.foodhyd.2012.01.004.
Extended European Search Report mailed Dec. 7, 2023 in corresponding EPO Application 20890751.9.

* cited by examiner

*Primary Examiner* — Pancham Bakshi
(74) *Attorney, Agent, or Firm* — Karen S. Canady; canady + lortz LLP

(57) ABSTRACT

A liquid embolic composition of natural polymers, water, and angiographic contrast agents improves neurovascular interventions, making them more reliable, safe, and affordable. The embolic material is made of a single component activated by blood calcium ion, which triggers coagulation, and that offers superior mechanical stability and does not cause fragmentation in the target vessel. The material retains superior long-term mechanical durability after deployment and provides sufficient visualization under fluoroscopy with iodine-based angiographic contrast compounds or other radiopaque compositions. Described herein are aqueous solutions that enable a high concentration gellan gum (greater than 0.5 wt %) to retain sol state even at the range of body temperature (30-40° C.). This discovery means that it is possible to increase the concentration of gellan gum without losing its inject-ability, yet significantly improve its mechanical stability after delivery.

16 Claims, 7 Drawing Sheets

LIQUID EMBOLIC MATERIAL COMPOSITION

This application claims benefit of U.S. provisional patent application No. 62/938,110, filed Nov. 20, 2019, the entire contents of which are incorporated by reference into this application.

BACKGROUND

Cerebrovascular disease is the fifth most common cause of death and the number one cause of disability in the United States. Hemorrhagic stroke, bleeding in the brain, are commonly caused by vascular malformation, such as brain arteriovenous malformation (bAVM) or by acquired vascular diseases such as brain aneurysm, dural arteriovenous fistula (dAVF) and others. Despite the remarkable advancement in the field of endovascular treatment, which is a new technology treating the cerebrovascular diseases from inside the vessels using catheters, these conditions remain to be serious diseases and it is partially due to the limitations of currently available devices and materials.

Liquid embolic material (LEM) is an important treatment tool used in the field of neuro-endovascular treatment. It plays a major role for the treatment of brain arteriovenous malformation (bAVM), dural arteriovenous fistula (dAVF) as well as intracranial tumors. The two major LEMs used in the current practice include 1) acrylic adhesive (e.g., n-butyl cyanoacrylate: nBCA) and 2) ethylene vinyl alcohol polymers (EvOH) dissolved in the organic solvent called dimethyl sulfoxide (DMSO) (Onyx® Embolic System). The latter, a non-adhesive LEM, was initially developed to overcome the limitation of acrylic adhesives, which has a strong adhesiveness causing the risk of catheter-entrapment during the procedure.

There are currently several different solutions (liquid embolic materials) to treat cerebrovascular diseases, e.g., bAVM, dAVF, and also in part, brain aneurysms (BA).

There remains a need for an embolic material offering sufficient mechanical durability without toxicity or such strong adhesiveness that causes catheter entrapment.

SUMMARY

The materials and methods described herein provide a liquid embolic composition of natural polymers, water, and angiographic contrast agents that improve neurovascular interventions, making them more reliable, safe, and affordable. The embolic material described herein is made of a single component activated by blood calcium ion triggered coagulation (BCTC) that offers superior mechanical stability and does not cause fragmentation in the target vessel. The material retains superior long-term mechanical durability after deployment, and provides sufficient visualization under fluoroscopy with iodine-based angiographic contrast compounds or other radiopaque compositions.

Described herein are aqueous solutions of "gellan gum" with higher concentration of 0.6-2.0 wt %, (compared to those of the prior art [see Liquid Embolic Agent Composition: WO2019163012; JP6383133; US2020-0009290A1], which range from 0.1-0.5 wt %). In the field of polymer engineering, it is a generally understood that the gellan gum solution of 0.5 wt % or higher concentration cannot retain a sol state at room temperature due to its sol-gel transition property. It will spontaneously form hydrogel in the absence of $Ca^{2+}$ ions, unless it is incubated in the higher temperature ca 90° C. Therefore, it is impossible for the material composition kept in a sol state at the range of usual body temperature ca 30-40° C.

In one embodiment, described herein is a composition comprising a gellan gum and a gelation suppressor. In some embodiments, the composition comprises 0.6-2.0 wt % gellan gum; 0.01-20 wt % low molecular weight polyols and/or amino acids (serving as a gelation suppressor); and 10-40 wt % angiographic contrast agent or other radiopaque material. In some embodiments, the composition comprises 0.8-2.0 wt % gellan gum; 3-10 wt % low molecular weight polyols and/or amino acids (serving as a gelation suppressor); and 10-40 wt % angiographic contrast agent or other radiopaque material. In some embodiments, the composition retains a sol state upon annealing to 30-40° C. In some embodiments, the composition is free of alginate. In some embodiments, the composition further comprises alginate. In some embodiments, the low molecular weight polyols are selected from the group consisting of glucose, mannose, glucitol, mannitol, ribose, arabinose, xylose, and other hexoses and pentoses, and sugar alcohols thereof. In some embodiments, the low molecular weight amino acids are selected from the group consisting of: glycine, alanine, valine, leucine, β-alanine, sarcosine, glutamate, aspartate, pyroglutamate, proline, serine, threonine, and their derivatives containing amino and carboxy functionalities thereof. Representative examples of derivatives include, but are not limited to, L-hydroxyproline, N,N-dimethyl glycine, and betain.

Also provided is a method of preparing a liquid embolic composition. In some embodiments, the method comprises combining, at 80-90° C.:
- (a) 0.6-2.0 wt % gellan gum solution,
- (b) 0.01-20 wt % low molecular weight polyols and/or amino acids; and
- (c) 10-40 wt % radiopaque material; or, alternatively,
- (a) 0.8-2.0 wt % gellan gum solution,
- (b) 3-10 wt % low molecular weight polyols and/or amino acids; and
- (c) 10-40 wt % radiopaque material.

Also provided is a composition prepared by the above method. Further described is a method of embolizing a target blood vessel in a subject. In some embodiments, the method comprises (a) introducing a catheter into the target blood vessel; and (b) injecting a composition of any one of claims 1 to 4 or 6 into the target blood vessel via the catheter. In some embodiments, step (b) is performed under fluoroscopy. In some embodiments, step (b) is performed until complete occlusion of the target blood vessel is confirmed. In some embodiments, the target blood vessel is a cerebral artery. In some embodiments, the target vessel is associated with a tumor. In some embodiments, the target vessel is associated with a brain arteriovenous malformation and/or a dural arteriovenous fistula.

Additionally, provided is a method of treating a vascular condition. The treatment method comprises deploying the method of embolizing a target blood vessel as described herein. Representative examples of a condition to be treated include, but are not limited to, a brain aneurysm, a tumor (intracranial or extracranial), a brain arteriovenous malformation, a dural arteriovenous fistula, and a brain bleed.

DETAILED DESCRIPTION

Figures 1, 2:
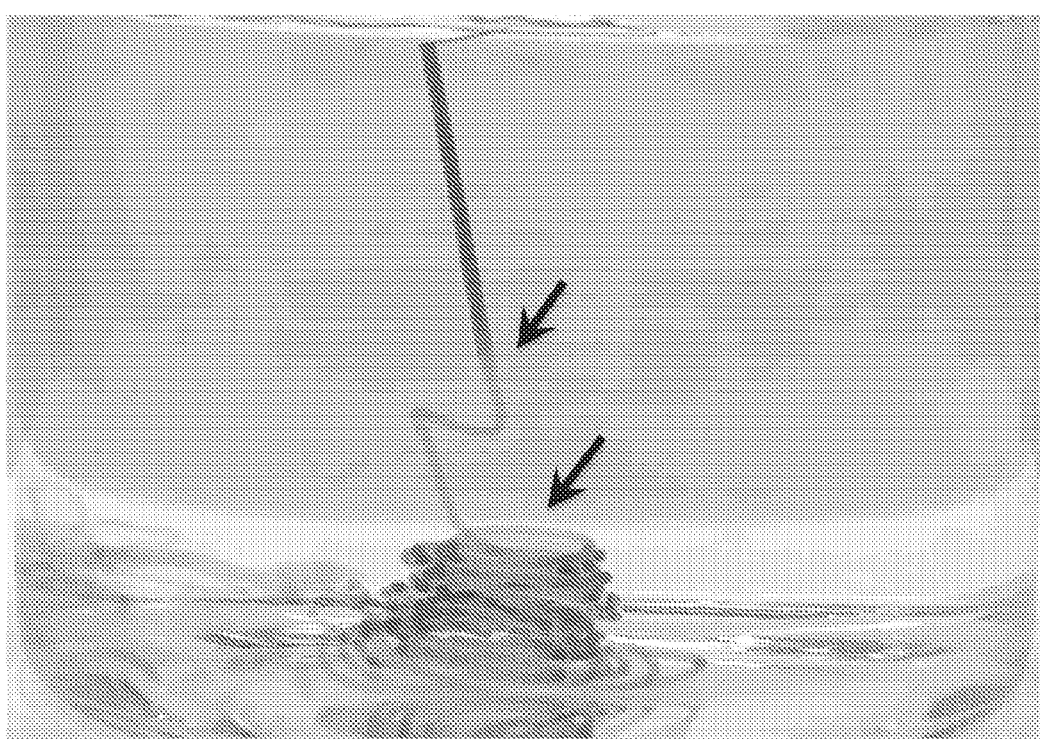
FIG. 1 is a digital photograph illustrating coagulation of gellan-based liquid embolic material (GBLEM) triggered by calcium ions in artificial blood plasma. The medium contains 150 mM NaCl, 20 mM Tris buffer (pH 8.0), and 5.0 mM CaCl$_2$. Upper arrow points to tip of microcatheter. Lower arrow points to gellan-based liquid embolic material (GBLEM) coagulated with Ca$^{2+}$ ions.
FIG. 2 provides the chemical structure of gellan gum (low acylated product).

The invention described herein is based on the unexpected discovery that several different types of polyhydroxylated, low molecular mass compounds, amino acids, and their derivatives enable a high concentration gellan gum (greater than 0.5 wt %) to retain sol state even at the range of body temperature (30-40° C.). This discovery means that it is possible to increase the concentration of gellan gum without losing its inject-ability, yet significantly improve its mechanical stability after delivery. This technology also renders the composite able to be combined with the iodine-based contrast materials along with other radiopaque materials, and activated by the BCTC.

Definitions

All scientific and technical terms used in this application have meanings commonly used in the art unless otherwise specified. As used in this application, the following words or phrases have the meanings specified.

As used herein, a term "low molecular weight" specifies any of compounds/substances having their molecular mass less than 1000 Dalton (Da).

As used herein, "polyols" refers to low molecular weight, polyhydroxylated organic compounds.

As used herein, "radiopaque materials" are agents used to visualize the embolization behavior of the GBLEM during surgical procedures. In this context, the term "radiopaque materials" includes angiographic contrast agents, metal particles, or other agents facilitating visualization.

As used herein, a "control" or "reference" sample means a sample that is representative of normal measures of the respective marker, such as would be obtained from normal, healthy control subjects, or a baseline amount of marker to be used for comparison. Typically, a baseline will be a measurement taken from the same subject or patient. The sample can be an actual sample used for testing, or a reference level or range, based on known normal measurements of the corresponding marker.

As used herein, a "significant difference" means a difference that can be detected in a manner that is considered reliable by one skilled in the art, such as a statistically significant difference, or a difference that is of sufficient magnitude that, under the circumstances, can be detected with a reasonable level of reliability. In one example, an increase or decrease of 10% relative to a reference sample is a significant difference. In other examples, an increase or decrease of 20%, 30%, 40%, or 50% relative to the reference sample is considered a significant difference. In yet another example, an increase of two-fold relative to a reference sample is considered significant.

As used herein, "pharmaceutically acceptable carrier" or "excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Compositions comprising such carriers are formulated by well-known conventional methods (see, for example, *Remington's Pharmaceutical Sciences,* 18th edition, A. Gennaro, ed., Mack Publishing Co., Easton, PA, 1990).

As used herein, the term "subject" includes any human or non-human animal. The term "non-human animal" includes all vertebrates, e.g., mammals and non-mammals, such as non-human primates, horses, sheep, dogs, cows, pigs, chickens, and other veterinary subjects. In a typical embodiment, the subject is a human.

As used herein, "a" or "an" means at least one, unless clearly indicated otherwise.

Methods of the Invention

Described herein are methods for preparation and use of a liquid embolic composition. In some embodiments, provided is a method of preparing a liquid embolic composition. In some embodiments, the method comprises combining, at 80-90° C.: (a) 0.6-2.0 wt % gellan gum solution, (b) 0.01-20 wt % low molecular weight polyols and/or amino acids; and (c) 10-40 wt % radiopaque material. In some embodiments, the method comprises combining, at 80-90° C.: (a) 0.8-2.0 wt % gellan gum solution, (b) 3-10 wt % low molecular weight polyols and/or amino acids; and (c) 10-40 wt % radiopaque material.

In some embodiments, the composition comprises 0.6-2.0 wt % gellan gum; 0.01-20 wt % low molecular weight polyols and/or amino acids (serving as a gelation suppressor); and 10-40 wt % angiographic contrast agent or other radiopaque material.

Examples of radiopaque materials include, but are not limited to, angiographic contrast agents and other agents facilitating visualization of the embolic material. Representative examples of radiopaque material include, but are not limited to: (i) water-soluble iodine-based organic compounds, such as iohexol isomers and iopamidol, which are the derivative of 5-amino-2,4,6-triode isophthalamide thereof at 17.5-40 wt %, and (ii) inorganic metal particle, such as tantalum powder at 10-15 wt %, which can be dispersed in the GBLEM. As (ii), other metal particles or colloidal derivatives can be employed while ensuring biocompatibility. The concentration of (i) and (ii) can be modified, depending on the preferred level of visibility under fluoroscopy.

Further described is a method of embolizing a target blood vessel in a subject. In some embodiments, the method comprises (a) introducing a catheter into the target blood vessel; and (b) injecting a composition as described herein into the target blood vessel via the catheter. In some embodiments, step (b) is performed under fluoroscopy. In some embodiments, step (b) is performed until complete occlusion of the target blood vessel is confirmed. In some embodiments, the target blood vessel is a cerebral artery. In some embodiments, the target vessel is associated with a tumor. In some embodiments, the target vessel is associated with a brain arteriovenous malformation and/or a dural arteriovenous fistula.

Additionally provided is a method of treating a vascular condition. The treatment method comprises deploying the method of embolizing a target blood vessel as described herein. Representative examples of a condition to be treated include, but are not limited to, a brain aneurysm, a tumor (intracranial or extracranial), a brain arteriovenous malformation, a dural arteriovenous fistula, and a brain bleed.

The liquid embolic material composition in the present invention is referred to as "gellan-based liquid embolic material (GBLEM)", because the active ingredient that entraps the blood calcium ion is gellan gum. In some embodiments, no alginate is present in the composition. This gellan-based liquid embolic material is characterized by its rapid coagulation process upon the contact with calcium ions in blood. The composition of the gellan-based liquid embolic material is prepared by combining a 0.8-2.0 wt % gellan gum solution, 3-10 wt % low molecular weight polyols, and 10-40 wt %, or, in some embodiments, 30-40 wt %, angiographic contrast agents (or other radiopaque materials) at 80-90° C. In some embodiments, the composition of the gellan-based liquid embolic material is prepared by combining a 0.6-2.0 wt % gellan gum solution, 0.01-20 wt % low molecular weight polyols and amino acids (or their derivatives), and 10-40 wt %, or, in some embodiments, 30-40 wt %, angiographic contrast agents (or other radiopaque materials) at 80-90° C. The mixture can retain the sol state upon annealing to 30-40° C., which is in a range of the body temperature.

In some embodiments, the material can be used as a liquid embolic material for the endovascular treatment of cerebrovascular diseases. In a representative example, a microcatheter is navigated through the vessel and placed in a target artery under fluoroscopy. In a representative example, after preparing the material solution, it is placed in a regular 1 mL syringe, which is connected to the microcatheter. The loaded gellan-based liquid embolic material is then slowly injected into the target vessel under fluoroscopy until complete occlusion of the target artery is confirmed. In general, the smaller the inner diameter of the microcatheter, the more resistance would be generated when injecting the material from the syringe. It was shown that the utilization of the gellan-based liquid embolic materials is possible using almost all sizes of conventional, single lumen microcatheters that are currently available in the medical device market. The GBLEM is adaptable for narrow profile microcatheters, such as Marathon™, for example, that can be used for neuro-interventional surgeries.

Kits

The invention provides kits comprising a set of ingredients as described herein, such as compounds and agents to be used in methods of the invention (including methods of preparing and administering the liquid embolic composition), and optionally, one or more suitable containers containing compounds and agents of the invention. Compounds and agents can be provided separately, ready for mixing and use, and optionally conveniently packaged to facilitate use in accordance with the methods described herein. In some embodiments, the kit includes printed materials instructing the preparation and use of the compositions described herein. Kits can optionally include a buffer, excipient, or other suitable medium.

In some embodiments, the kit comprises a composition as described herein. In some embodiments, the kit comprises elements of the composition separately, to be prepared subsequently. For example, the kit can comprise a first container containing a 0.6-2.0 wt % gellan gum solution, a second container containing 0.01-20 wt % low molecular weight polyols and amino acids (or their derivatives), and a third container containing 10-40 wt %, or, in some embodiments, 30-40 wt %, angiographic contrast agents (or other radiopaque materials). The kit optionally further comprises instructions for preparing a composition in accordance with the methods described herein.

EXAMPLE EMBODIMENTS

Embodiment 1) A composition comprising: (a) 0.8-2.0 wt % gellan gum; (b) 3-10 wt % low molecular weight polyols and/or amino acids; and (c) 10-40 wt % radiopaque material.

Embodiment 2) The composition of embodiment 1, wherein the composition retains a sol state upon annealing to 30-40° C.

Embodiment 3) The composition of embodiment 1, which is free of alginate.

Embodiment 4) The composition of embodiment 1, further comprising alginate.

Embodiment 5) The composition of embodiment 1, wherein the low molecular weight polyols are selected from the group consisting of: D-glucose, D-mannose, glucitol, mannitol, ribose, arabinose, xylose, and other hexoses and pentoses, and sugar alcohols thereof.

Embodiment 6) The composition of embodiment 1, wherein the low molecular weight amino acids are selected from the group consisting of: glycine, alanine, valine, leucine, 3-alanine, sarcosine, glutamate, aspartate, pyroglutamate, proline, serine, threonine, and their derivatives containing amino and carboxy functionalities thereof.

Embodiment 7) A method of preparing a liquid embolic composition, the method comprising combining, at 80-90° C.: (a) 0.8-2.0 wt % gellan gum solution, (b) 3-10 wt % low molecular weight polyols and/or amino acids; and (c) 10-40 wt % radiopaque material.

Embodiment 8) A composition prepared by the method of embodiment 7.

Embodiment 9) A method of embolizing a target blood vessel in a subject, the method comprising: (a) introducing a catheter into the target blood vessel; and (b) injecting a composition of any one of embodiments 1 to 6 or 8 into the target blood vessel via the catheter.

Embodiment 10) The method of embodiment 9, wherein step (b) is performed under fluoroscopy.

Embodiment 11) The method of embodiment 9 or 10, wherein step (b) is performed until complete occlusion of the target blood vessel is confirmed.

Embodiment 12) The method of any of embodiments 9 to 11, wherein the target blood vessel is a cerebral artery.

Embodiment 13) composition comprising: (a) 0.6-2.0 wt % gellan gum; (b) 0.01-20 wt % low molecular weight polyols and/or amino acids; and (c) 10-40 wt % radiopaque material.

Embodiment 14) the method of any of embodiments 9 to 12, wherein the composition is the composition of embodiment 13.

EXAMPLES

The following examples are presented to illustrate the present invention and to assist one of ordinary skill in making and using the same. The examples are not intended in any way to otherwise limit the scope of the invention.

These examples demonstrate that several different types of polyhydroxylated, low molecular mass compounds, amino acids, and their derivatives enable the high concentration gellan gum (greater than 0.5 wt %) to retain sol state even at the body temperature range (30-40° C.). In other words, it is possible to increase the concentration of gellan gum without losing its inject-ability, yet significantly improve the mechanically stability after delivery. This technology also renders the composite to be combined with the iodine-based contrast materials along with other radiopaque materials, and activated by the BCTC.

Example 1: Preparation of Compositions: Components and Functions

This example describes preparation of an exemplary composition. In this example, all of the components of the gellan-based liquid embolic material (GBLEM) are water-soluble substances, and gellan is responsible for the blood calcium-triggered coagulation (BCTC) principle.
BCTC-Responsible Polymer, Qellan Gum—the Elevated Concentration Gellan gum has been registered as a Part 172 "Food Additives Permitted for Direct Addition to Food for Human Consumption", 21eCFR172.662 by the U.S. Food and Drug Administration (FDA) [US Food and Drug Administration (FDA): Food Additives Status List; Gellan Gum—MISC, REG, As a stabilizer & thickener; (See specs in 172.665), Electronic Code of Federal Regulations (21eCFR172.665) (current as Jun. 10, 2019)], and currently there is no security alert issued to gellan gum at least since 2006 as described in a Technical Evaluation Report by USDA. Gellan gum has not yet been approved for medical and pharmaceutical uses. However, given the federal regulation history of this material, it is likely to have chemically and biologically inert profiles to the human body.

Gellan gum can be applied as a stabilizer and thickener for food products, including jams, jellies, low-fat spreads, microwavable foods, and structured foods as indicated in [US Department of Agriculture, Technical Evaluation Report (Feb. 10, 2006)], the formulations of which involve this polysaccharide typically at the concentrations above 1%, plus 10% calcium chloride, if the mechanical property of the food produced needs to be stabilized.

The hydrogel texture of gellan gum, hence, forms instantly upon the addition of divalent cations, otherwise the elevated concentration of the polysaccharides (commonly recognized as greater than 0.5 wt %) can induce a spontaneous gelation even in the absence of divalent cations. Usually the blood calcium concentration are in a range of 2.5 mM-5.0 mM, which corresponds to $1.0 \times 10^{-3}$-$2.0 \times 10^{-3}$%.

When considering the application of this material for endovascular treatment, administrating the gellan gum followed by relatively high concentration (10%, for example) of calcium is not feasible because the sudden increase of the blood calcium concentration can cause systemic problems. Therefore, the reinforcement of the gellan coagulates or hydrogels in the blood vessel is conclusively achieved through the elevated concentration of the polysaccharide added to the GBLEM.

The option indicated above, the elevated concentration of gellan gum, consequently draws a trade-off: the GBLEM is not injectable through the micro-catheter lumen, due to a spontaneous, calcium-free gelation at the concentration of gellan gum above 0.5%, which is the upper limit as claimed in the patent specification in the prior art (alginate-based LEM [WO2019163012]).

The inventors have found a solution for the trade-off, by adding the gelling suppressor compounds to the GBLEM.
Gelling Suppressor and Thixotropy Reducers—Polyols and Choices A phenomenon that low molecular weight, dimeric or monomeric sugars often inhibit gelation of the high molecular weight polysaccharides has been known since several decades ago in the food processing industry. The reference [Sucrose as a gelation inhibitor of commercially frozen papaya puree, Harry Y. Yamamoto and Winfred Inouye, Technical Progress Report No. 137, an archive from Hawaii Agricultural Experiment Station, College of Tropical Agriculture, University of Hawaii, January 1963] is a typical example that indicates utilization of a dimeric sugar compound, sucrose ($\beta$-D-fructofuranosyl-$(2{\rightarrow}1)$-$\alpha$-D-glucopyranoside), for the fluidity improvement of a fruit homogenate, in which intermolecular association of high molecular mass pectin-related polysaccharides potentially induce the gelation via formation of hydrogen bonds or physical entanglements among the polymeric molecular chains.

Thus, low molecular weight, polyhydroxylated organic compounds (polyols) prevent the polymer chains from interacting with each other in a dose-dependent manner along with the molar stoichiometry of sugar residues embedded in the pectin chain against the free sucrose molecules, as seen in reference [Sucrose as a gelation inhibitor of commercially frozen papaya puree, Harry Y. Yamamoto and Winfred Inouye, Technical Progress Report No. 137, an archive from Hawaii Agricultural Experiment Station, College of Tropical Agriculture, University of Hawaii, January 1963], implying a mechanism that excess sucrose molecules frequently interrupt the direct association of polymer chains, with mediating water molecules in between.

The interruption effect of polyols mentioned above can also be adopted in the case of gellan gum in order to retain the GBLEM in a sol and fluid state before injection into the vascular environment, where the contact between gellan and calcium ions triggers the coagulation of the polysaccharide molecules to form a rigid hydrogel. The hydrogelation of gellan gum solution has been thoroughly investigated [Gelation of gellan—A review, Edwin R. Morris, Katsuyoshi Nishinari, Marguerite Rinaudo, Food Hydrocolloids 28: 373-411 (2012)], and currently, there are two different models to demonstrate the gelation process in the absence of calcium ions, both of which involve two steps of different phase transition upon annealing the solution from the dissolution temperature at approximately 90° C., then descending the temperature around 20° C.; the first step is a fibril formation to increase the solution viscosity (45-55° C. transition 1), followed by another step as inter-fibrillar association (15-25° C., transition 1l), to form a macroscopic hydrogel texture with almost no fluidity.

Polyol molecules probably retain the physicochemical state of the gellan molecules in aqueous solution in between the phase transitions I and II, which means that the polyol molecules interrupt the fibrils interaction with each other. In one embodiment, when 1.2 wt % gellan aqueous solution containing 9 wt % D-glucose (a polyol) was prepared via dissolution at 95° C., during the annealing time course, the viscosity gradually increased and the homogenous solution turned to a transparent, thixotropic fluid at ca 30° C. "Thixotropy" is a term of rheology, which defines a fluid that has a time-dependent viscosity, and is distinguished from the "shear thinning (pseudoplastic) fluid", which can instantly gain up the storage modulus as the shear stress is released, likely seen in reference [An injectable shear-thinning biomaterials for endovascular embolization, Reginald K. Avery, Hassan Albadawi, Mohsen Akbari, Yu Shrike Zhang, Michael J. Duggan, Dushyant V. Sahani, Bradley D. Olsen, Ali Khademhosseini, Rahmi Oklu, Science Translational Medicine 8: 365ra156 (12 pages) (2016)].

Figure 3:
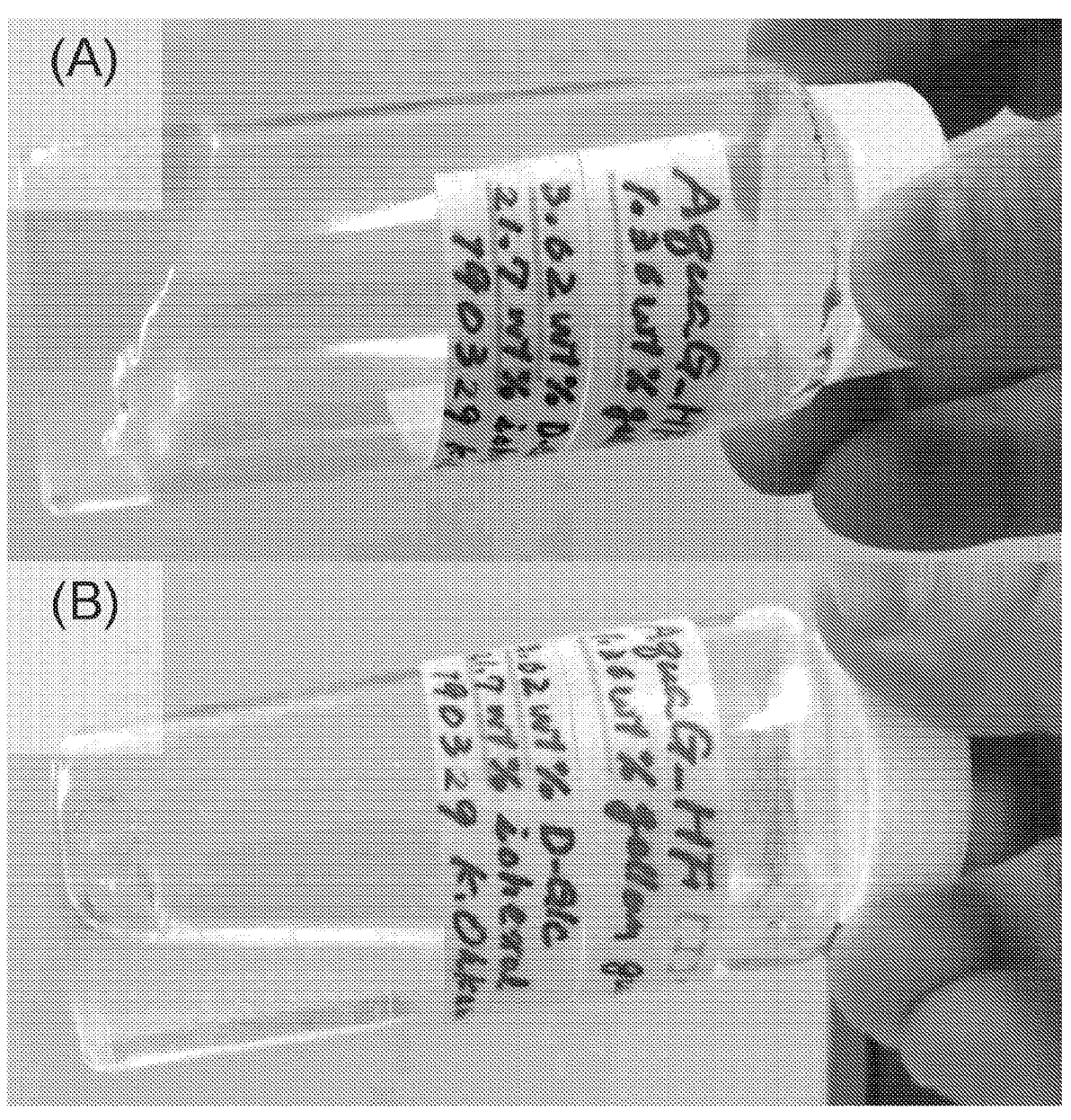
FIG. 3 is a pair of digital photographs depicting the rapid recovery of fluidity of GBLEM. (A) GBLEM stored at 4° C. is a viscous fluid; and (B) after a flash heating, GBLEM shows a rapid recovery of fluidity.

In consequence, thixotropic behavior corresponds to an intermediate state between a non-Newtonian fluid and plastic sol, as well as exhibits a non-zero time in decreasing the fluidity gradually. In the case of the GBLEM containing 1.36 wt % gellan and 3.6 wt % D-glucose, thixotropic behavior was observed around 30-40° C. with a highly viscous nature but turning into a smooth sol when shaken, while, as increasing the concentration of D-glucose up to 9-10 wt %, the GBLEM mostly retains fluidity around 30-40° C. the observation of which indicates that D-glucose reduces the thixotropic property. This also suggests that D-glucose molecules reversibly associate and dissociate with the gellan fibrils in an intermediate state between the phase transitions I and II, and as a result of the equilibrium, it makes the GBLEM fully injectable via microcatheter even in the presence of a lowered concentration of D-glucose as 3.6 wt %, by a conventional microwave oven heating just for a couple of seconds, as demonstrated in FIG. 3.

In the presence of 9 wt % D-glucose as a pre-injection gelling suppressor, 1.2 wt % gellan aqueous solution (plus 0.1 wt % blue-dextran for visualization) instantly coagulates to form a hydrogel upon contact with an artificial blood plasma (0.15 M NaCl, 20 mM Tris•HCl, pH 8.0, 5.0 mM CaCl$_2$), as indicated in FIG. 1.

The polyols already tested as gelling suppressors are monomeric hexoses, D-glucose and D-mannose, and their corresponding sugar alcohols, glucitol and mannitol, in the range of 3.0-10 wt %. As well, the polyols are potentially selected one from a group of other hexoses, pentoses, and corresponding sugar alcohols, including ribose, arabinose, and xylose. The polyol chemicals can be selected to avoid stimuli that induce any physiologically negative situations, and the polyol concentration is adjustable for regulation of the blood osmotic pressure.

Angiographic Components—how to Adjust the Radiopacity

Any of water-soluble angiographic compounds are adaptable to the GBLEM. Two of conventional iodine-type angiographic chemicals, iohexol isomers and iopamidol are commercially available chemicals for the radiopaque components. Omnipaque™ and Iopamiron™ are trademarks of frequently used angiographic contrast agents and contain iohexol isomers and iopamidol, respectively as the radiopaque compounds, of which end products are provided as "ready-to-use", transparent solutions in plastic bottles. Both iohexol isomers and iopamidol are derivatives of N-acyl-5-amino-2,4,6-triode isophthalamide, and the iodine contents in Omnipaque™ and Iopamiron™ are the radiopacity intensity indicators, which are clearly marked, for example "Iopamiron 300", on the bottle labels, for which the example indicates that the iodine content [I] is equivalent to 300 mg/mL.

While the [I] is an "equivalent" value just for the content of iodine elements in the end product, the actual concentration of iohexol isomers or Iopamidol are separately calculated on the basis of the iodine mass percentages in each of the contrasts' molecular formulae. For instance in a case of Omnipaque300, the iodine mass percentage (% I) in the molecular formula weight of Iohexol isomer (Fw=821 g/mol) is 46.4%1, which leads to the solute concentration as [iohexol]=300/0.464 mg/mL=647 mg/mL=0.79 mol/L (M). Iopamiron300 also has an iopamidol (Fw=777 g/mol) concentration of [iopamidol]=612 mg/mL=0.79 M.

The concentrations, [iohexol] and [iopamidol] as indicated above for the cases of [I]=300 mg/mL, correspond to the solute mass percentages as 64.7 wt % and 61.2 wt %, respectively. Omnipaque contains a subcomponent, 0.1 mg/mL of disodium calcium ethylenediamine-N,N,N',N'-tetraacetate (EDTA•2Na•Ca, aka calcium disodium edetate, Fw=374 g/mol), and the calcium ion concentration is [Ca$^2$]=0.27 mM. When the gellan gum powder is added to Omnipaque solution at 90° C., the gellan gum was not completely dissolved at 0.8-1.3 wt %, due to the presence of calcium disodium edetate, indicating that this approach did not work to prepare the GBLEM with satisfactory radiopacity under fluoroscopy. Calcium free medium, therefore, is used to dissolve gellan gum at the preferred concentration.

Iohexol or iopamidol has to be directly dissolved in hot distilled (calcium free) water, but here is also a trade-off. The highly elevated mass percentage of iohexol, for instance as seen in that [1]=300 mg/mL is equal to [iohexol]=64.7 wt %, leaves the fraction of 35.3 wt % mass ratio for other components including gellan, polyols, and water as the medium/solvent of the GBLEM. If the mass percentage of gellan gum and polyol occupy 1.3 wt % and 10 wt %, respectively, available room for water is just 24 wt %, in which the mass ratio between gellan and water is 1.3:24, meaning that the net concentration of gellan is 5.1 wt %. Under such a net concentration of gellan gum, the gelling suppression action of polyols no longer works, and, in fact, the trials for preparing the GBLEM as described above resulted in a composite having no fluidity at 30-40° C., which means that the composite was not injectable.

Figure 4:
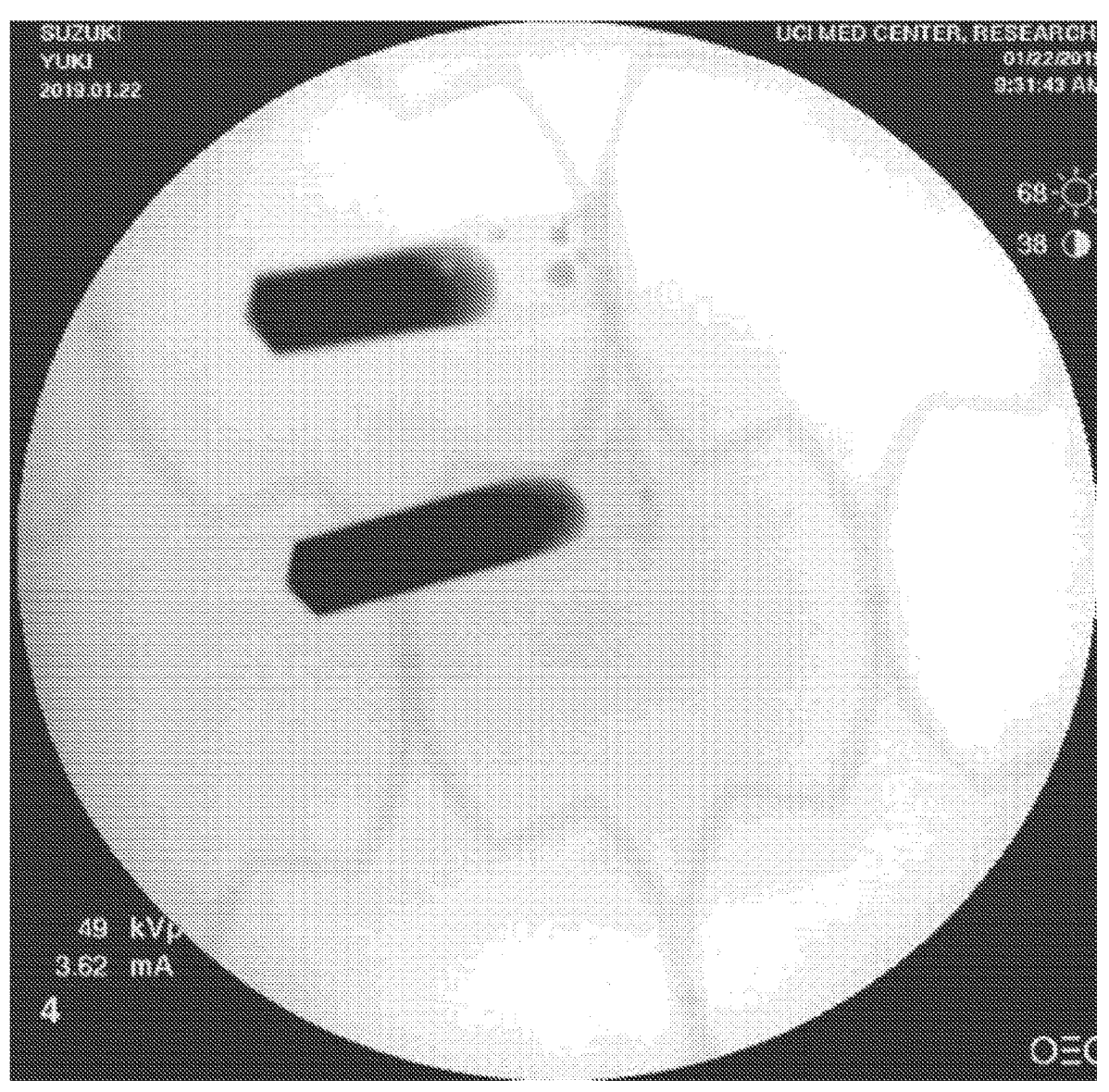
FIG. 4 is a fluoroscopy image demonstrating a comparison of radiopacity of GBLEM (upper tube) containing iohexol ([I]=230 mg/mL) and Omnipaque300 (lower tube) ([I]=300 mg/mL).

The inventors finally found that the injectable composite can be prepared only when the iohexol concentration does not exceed to 49 wt %, which corresponds to [I]=230 mg/mL as the maximum value of the radiopacity indicator. As a conclusion, working mass percentage of iodine based angiographic agents is ranging from [I]=100-230 mg/mL, in the presence of 0.8-1.3 wt % gellan gum and 3-10 wt % of polyols. The comparison of radiopacity is demonstrated in FIG. 4.

Figure 5:
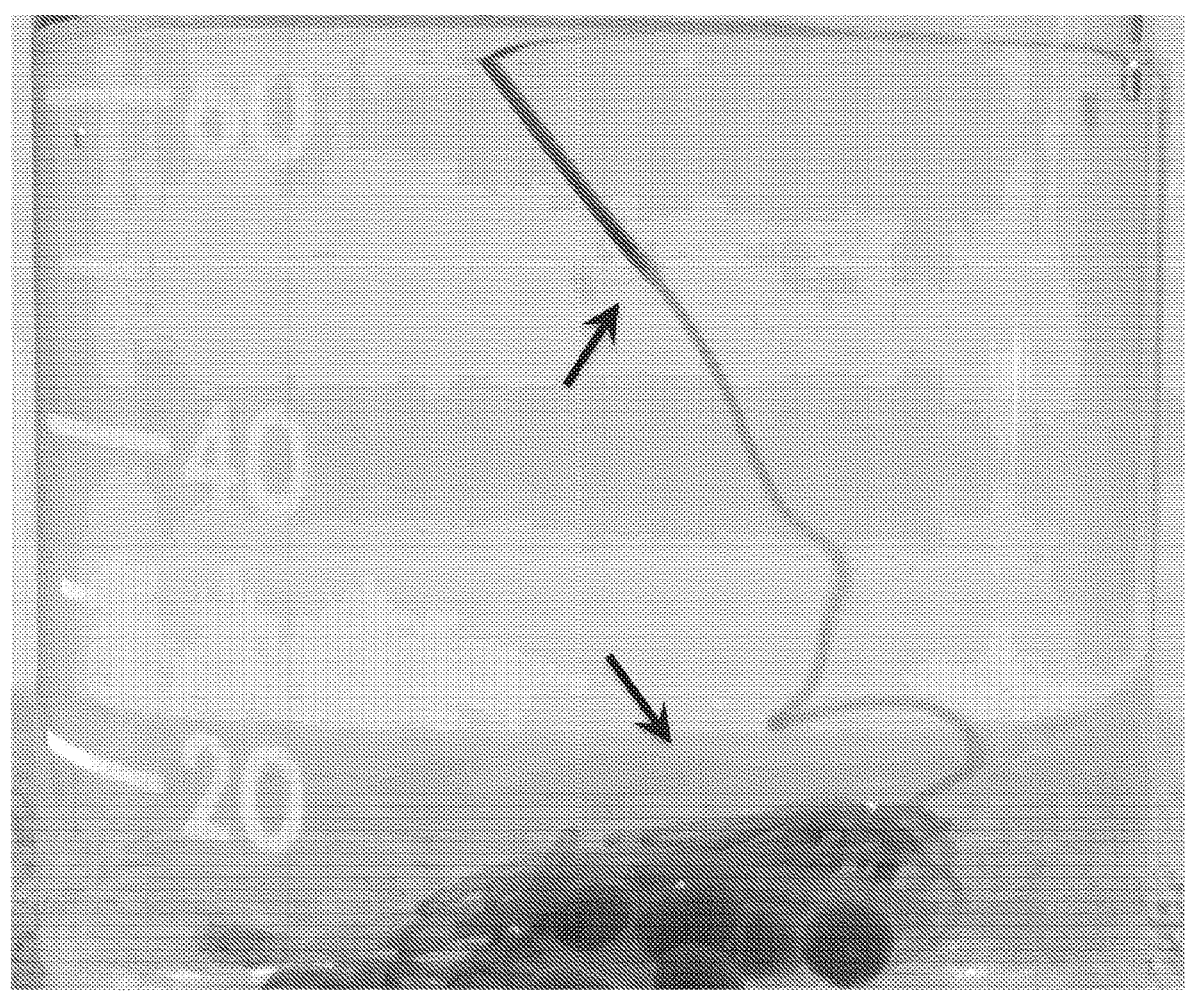
FIG. 5 is a digital photograph showing GBLEM mixed with tantalum particles and exhibiting rapid coagulation upon contact with calcium ions. The medium contains 150 mM NaCl, 20 nM Tris buffer (pH 8.0), and 5.0 mM CaCl$_2$. The upper arrow points to the tip of the microcatheter. The lower arrow points to coagulated GBLEM mixed with tantalum (black) particles.

Another approach to exert the radiopacity of the GBLEM is to add fine tantalum (Ta) powder to the composite. The mass ratio of Ta powder is 8-12 wt % and the BCTC principle is still working by an observation of instant hydrogelation of the GBLEM (gellan 1.2 wt %, D-glucose 9 wt %), as seen in FIG. 5. Other heavy metals, commonly used in the field of endovascular devices, such as tungsten, platinum, gold, or cobalt-chrome, can be also potentially used as radiopaque materials. Bismuth-containing compounds, for instances, bismuth oxides or bismuth citrates, and can also be selected as the radiopaque materials, which do not inhibit the BCTC principle.

Potential Subcomponents to Modify the Gelling Rate and Injectability

The fibril structure of gellan gum is formed via a double helix type association of two parallel chains of the molecule, where the pitch of the rotational periodicity is ca 5.6 nm [Gelation of gellan—A review, Edwin R. Morris, Katsuyoshi Nishinari, Marguerite Rinaudo, Food Hydrocolloids 28: 373-411 (2012)]. Formation of the ordered structure is potentially interrupted when coexisting high polymers of another kind have an electrically neutral nature. A super high molecular weight preparation of glucomannan or xanthan gum is the candidate as fibril formation inhibitors, leading to modify the gelling rate at 30-40° C. for a better inject-ability due to a lowered viscosity of the GBLEM. A highly acylated grade preparation, so called "native gellan gum" is also a candidate for modifying a gelling property of the GBLEM. The GBLEM containing native gellan gum was tested in an animal experiment, and it was found that the native gellan gum can improve mechanical durability of the material after deployment in a blood vessel. This result is described later in detail (animal experiments using rabbit renal artery).

Example 2: Preparation of GBLEM, Dissolution Sequences of Components

This example describes gellan gums as an active ingredient for the BCTC principle, polyols and amino acids as phase transition modifiers, and dissolution of the components of GBLEM in water.

Following are commercially available gellan gums, which are specified with the identical registry numbers of Chemical Abstract Service (CAS RN): a reagent grade of gellan gum (deacetylated, CAS RN, 71010-52-1) for plant tissue culture (FujiFilm Corporation, Japan); other trade names, Kelcogel® (CP Kelco, US, Inc., CAS RN, 71010-52-1), Geirite (FujiFilm Corporation, CAS RN, 71010-52-1), Phytagel™ (Sigma-Aldrich, CAS RN, 71010-52-1), or CultureGelm (PhytoTechnology Laboratories, CAS RN, 71010-52-1). The GBLEM in the present invention can be prepared using gellan gums listed above.

Polyols and Amino Acids as Phase Transition Modifiers:

Any of reagent grades of the monomeric sugar-based polyhydroxylated compounds (polyols) can be adopted for suppressing gelation of the GBLEM before injection into the artificial blood plasma and endovascular environment. The polyols are selected from at least one kind of the commercially available monomeric hexoses (D-glucose, D-mannose, and D-galactose), pentoses (D-ribose, D-arabinose) and the corresponding sugar alcohols, D-glucitol, D-mannitol, and so on. These polyols are water-soluble, and hence can be combined with the gellan gum preparations as above. The polyols are also selected and combined with gellan gum, as long as its biocompatibility in the human body is confirmed.

Several kinds of low molecular weight amino acids are also effective to retain the fluidity of GBLEM before injection. Glycine, sarcosine (N-methyl glycine), N,N-dimethyl glycine, betaine (N,N,N-trimethyl glycine), alanine, proline, trans-4-hydroxyproline (and the isomers), β-alanine, glutamate, aspartate, pyroglutamate, serine, threonine are confirmed to be capable of suppressing gelation for the GBLEM. The common feature of the amino acids is that the compound has one primary, secondary, tertiary, or quaternary amino group and one carboxyl group in the molecular formulae. The primary, secondary, tertiary, and quaternary amino groups of these compounds can interact with the carboxyl group on the glucuronic acid residue in the gellan's molecular backbone, resulting in the inhibition of the filament formation between gellan molecules via the glucuronic acid residues. The N-end amino group on the peptides, hence for instance serylserine, are also able to suppress the gelation of GBLEM. The concentration of the amino acids or peptides in the GBLEM can be set from 0.01-20 wt %, where any of physiological stimuli to the human body will be avoided.

The amino acids (or peptides) can be combined with polyols to enhance the effects on the gelation suppression.

Preparation of GBLEM—Dissolution of the Components in Water

The concentrations of the components are represented in weight percentage (wt %). As mentioned in the roles of the gelation suppressor, polyols and amino acids have to be dissolved in water prior to the dissolution of gellan gum. A typical procedure of the GBLEM preparation involves the following steps. Distilled and deionized water (DDW) (7.00 g) is placed in a glass vial and D-glucose (0.5 g) was dissolved at room temperature. Gellan gum (0.12 g) was added to the solution, and with stirring, the dissolution temperature is elevated to 85-90° C. It typically takes for a couple of hours for complete dissolution of gellan gum, and then finally iohexol (2.38 g) is added to the solution. The final concentrations in the total mass of 10 grams are 1.2 wt % for gellan gum, 5 wt % for D-glucose, and 23.8 wt % for iohexol ([I]=110 mg/mL). After annealing to 35-40° C., the solution retains the fluidity.

GBLEM can be prepared in the presence of sodium alginate [WO2019163012] insofar as the fluidity of the composite at the temperature above is fully retained to be injectable from a microcatheter. For some embodiments, gellan gum (1.0 wt %), alginate (0.7 wt %), either L-serine or L-hydroxyproline (amino acids, 0.9 wt %), either sarcosine or betaine (amino acids, 0.6 wt %), either D-glucitol or D-mannitol (polyols, 2.0 wt %), and iohexol (contrast, 12.0 wt %) in DDW. These composites are also used in combination with metal powders (contrasts, 5-15 wt % towards composites).

In some embodiments, the concentrations of the components are: gellan, 0.8-2.0 wt %, or, in some embodiments, 0.6-2.0 wt %; polyols or amino acids, 3.0-10.0 wt %, or in some embodiments, 0.01-20 wt %; contrast agent, 17-36 wt %. Super high molecular weight glucomannan, pullulan, xanthan gum, and highly acylated gellan gum can also be added at concentrations ranging from 0.1-0.5 wt % as the elasticity modifiers for the GBLEM hydrogel after injection into the artificial blood plasma in vitro or blood vessels in vivo.

Example 3: Post-Preparation Procedures, Vialing and Sterilization

This example describes GBLEM prepared as above that is dispensed into small volume vials, typically as of 2.0-5.0 mL. After dispensing, the GBLEM in the small volume vials can be sterilized using a conventional autoclave instrument. The sealed vials can be stored at room temperature for a couple of months. Without the sterilization, biological contamination can occur over time in storage.

Example 4: Embolic Material Performance in Animal Studies

Animal model #1: rabbit model for the evaluation of liquid embolic materials

Kidney is one of the most vascular rich organs in the body of vertebrate animals. Therefore, in many animal models, renal artery and kidney have been commonly used for the evaluation of the endovascular devices. For instance, the kidney tissue can simulate a vascular rich tumor tissue and the renal artery can simulate the feeding artery of the tumor itself. In the preliminary studies, we used the renal artery of rabbit to evaluate the performance of the prototype materials under fluoroscopy.

Animal model #2: swine model for the evaluation of liquid embolic materials

*Rete mirabile*, which is a unique vascular meshwork observed in the skull base of swine, has been used for evaluating the liquid embolic materials for the treatment of brain arteriovenous malformation (bAVM). A microcatheter is placed in the artery called ascending pharyngeal artery of a swine, and the tested liquid embolic material is injected to the bAVM model to evaluate its mechanical performance.

The prototypes of GBLEM have been tested using these animal models.

(a) Evaluation Using Rabbit Renal Arteries

Experiment #1, Animal: New Zealand rabbit

Weight: Approximately 3000 g. (non-survival experiment)

GBLEM used: gellan gum, 1.34 wt %; D-glucose, 3.6 wt %; [1]=140 mg/mL (iohexol)

Endovascular Procedure (femoral artery approach)

Anesthesia induction, IV route placement on the left ear vein (24G angiocath), was performed with an induction dose (Ketamine 1 mL (100 mg)+Xylazine 0.75 mL (75 mg)). The IM injection of anesthetic agents (Ketamine 0.5 mL+Xylazine 1.0 mL cocktail) was given 0.25 mL in every 30 min for the maintenance of anesthesia. A 3 cm skin incision on the right femoral artery was made to expose the femoral artery and vein complex. The artery and vein were then separated by a blunt dissection. Using the 5-0 suture, a distal side of the exposed artery was ligated.

A slight tension was given on the 5-0 suture placed at the distal femoral artery. After giving papaverine for dilation of the vessel, a small arteriotomy was made by using the micro scissors. After inserting the guidewire of the micro-puncture kit in the femoral artery, the tip of the guidewire was placed at the mid abdominal aorta. A 4F micro-puncture kit sheath was inserted, and the back flow was confirmed. The micro-puncture kit was fixed to the vessel by a ligation with the 5-0 suture, as well as making another ligation to further stabilize the micro-puncture kit. The micro-puncture kit was connected to a Y-connector, which is filled with heparinized saline.

Delivery of the Liquid Embolic Material (GBLEM)

An Echelon 10 microcatheter was advanced over the Synchro 10 micro-wire and placed at the mid abdominal aorta. Angiogram was performed, and then the tip of the catheter was placed slightly proximal to the renal artery, and angiogram was repeated. By a road-mapping technique, the microcatheter was navigated into the left renal artery, and a selective angiography was performed.

Angiographical Results of the Left Renal Artery Occlusion

Under digital subtraction angiography (DSA), the GBLEM was injected into the left renal artery. The first 0.2 mL of the GBLEM filled out the dead-space of the microcatheter, then the injected material started filling the target artery. The injection was continued to reach the volume of 0.5 mL until a reflux of the GBLEM was observed, and then the injection was stopped. Under DSA, it was observed that the cast of injected material being pushed into the distal segment of the renal artery (distal migration) by the blood flow. Therefore, the injection was resumed. Upon an additional injection of the GBLEM of 0.2 mL, a reflux of the injected material was observed again. This time, no distal migration was found, and additional 0.2 mL volume was injected to confirm sufficient filling in the proximal segment of the renal artery but not a reflux into the abdominal aorta.

The catheter was pulled down to the distal abdominal aorta and completely removed.

The Echelon 10 microcatheter was flushed and cleaned with heparinized saline. The catheter was re-inserted, advanced over the Synchro 10 micro-wire and placed at the mid abdominal aorta. Angiogram was performed to confirm a complete occlusion of the left renal artery.

Angiographical Results of the Right Renal Artery Occlusion

Next, the tip of the catheter was placed in the proximal segment of the right renal artery, and angiogram was performed to obtain a road-mapping image. Under DSA, the GBLEM was slowly injected into the right renal artery. The first volume of 0.25 mL filled out the dead-space of the microcatheter, and when the injection was continued to reach a total volume of 0.5 mL until the reflux was observed, then the injection was stopped. Similar to the findings seen on the left side, distal migration of the injected material was observed, however, additional injection of the GBLEM (0.2 mL) showed a filling of the artery followed by reflux again, without no distal migration. Injection was stopped once the reflux into the abdominal aorta was found upon additional injection (0.2 mL) of the GBLEM. The catheter was pulled down to the distal abdominal aorta, and the endovascular procedure was completed. No catheter entrapment was observed.

The animal was euthanized by administrating the intravenous injection of Euthasol.

Experiment #2: Animal: New Zealand rabbit

Weight: Approximately 5.5 kg. (survival experiment)

GBLEM used: 0.15 g (1.5 wt %) gellan gum, 0.02 g (0.2 wt %) GC-HA (highly acylated preparation, so called native gellan gum), D-solbitol (aka D-glucitol, a sugar alcohol of D-glucose) 0.5 g (5.0 wt %), and 0.5 g (5.0 wt %) β-alanine were dissolved in deionized/distilled water (DDW, 8.83 g; total mass 10.0 g) at 80° C. for 72 hours, and then, an aliquot of this solution was mixed with 0.1 g Ta powder to a final volume of 1.0 mL.

Endovascular Procedure (Femoral Artery Approach)
Implantation of the GBLEM in the Left Renal Artery The same surgical and endovascular procedures described above were performed.

This time, one rabbit was subjected to a survival experiment. Immediately after the injection of the GBLEM into the left renal artery, post procedure angiogram was performed, which showed complete occlusion of the left renal artery. The catheter was removed without catheter entrapment. The wound in the left femoral region was closed layer to layer, and the animal was kept alive for long term evaluation.

Angiographical Evaluation Followed by Harvesting the Treated Artery

Two weeks after the embolization of the left renal artery, the animal was brought back to the lab, and the angiogram was performed using the left femoral artery access to inspect the status of previously treated vessel. The angiographical results showed persistent occlusion of the renal artery as well as no contrast filling in the capillary phase in kidney.

Day 0 (Injection of the material): A prototype of gellan based liquid embolic material was injected into the left renal artery of rabbit (5 kg). The renal arty was used to simulate the feeding artery of tumor like lesions.

Figure 6:
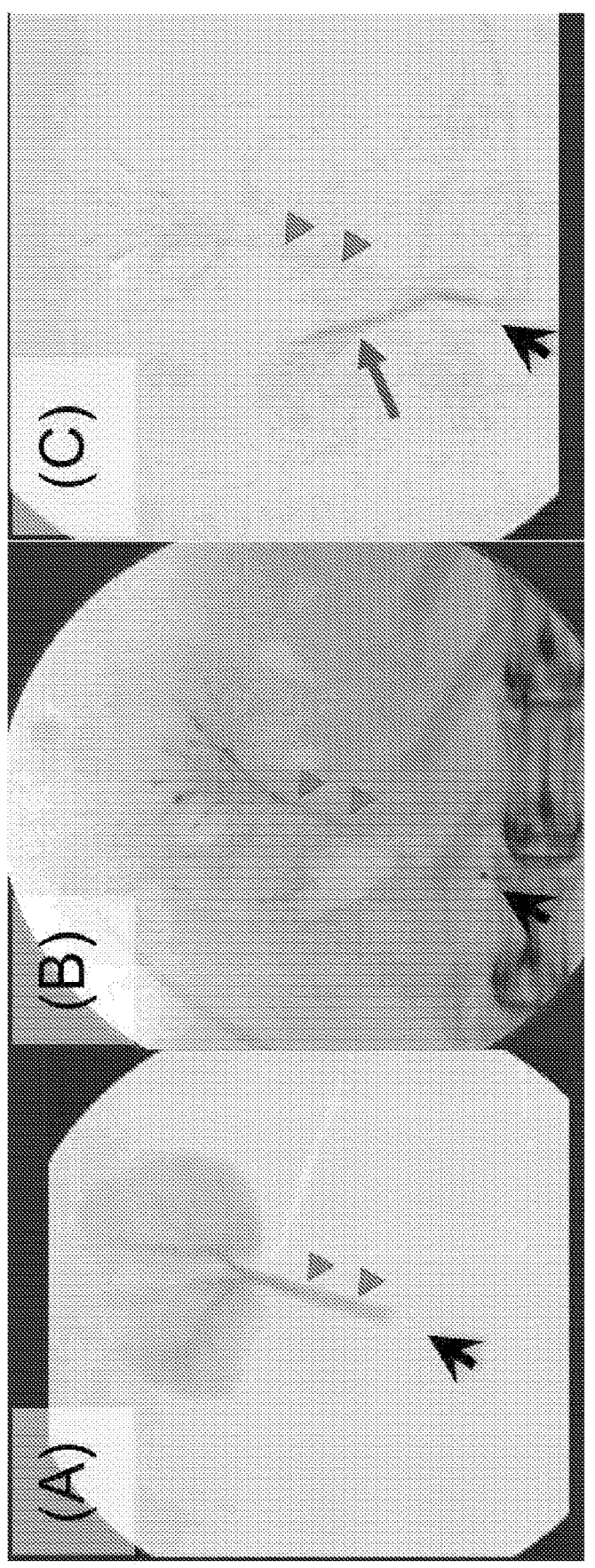
FIG. 6 is a series of radiographs showing evaluation of long term durability of the embolic material using a rabbit model. Panel (A) shows contrast injection using digital subtraction angiography (DSA) before occlusion. In all three panels, the lower arrow points to tip of microcatheter, and the paired arrowheads point to renal artery. Panel (B) shows GBLEM+tantalum cast seen under fluoroscopy at two weeks after occlusion. Image shows that cast was retained in branches and the main trunk. Panel (C) shows contrast injection in the treated renal artery using digital subtraction angiography (DSA) two weeks after treatment. Image shows that contrast flows into the adrenal artery (large arrow at left of center). The main trunk and branches of the renal artery remained occluded by GBLEM.

Day 14 (Follow-up Angiography followed by harvesting of the treated tissue): The left shows the pre-treatment angiogram of the left renal artery (FIG. 6A). Note the contrast filling in the main trunk of the renal artery (paired arrowheads) followed by the capillary brush of renal tissue is seen. The center shows a fluoroscopic image at Day 14. The cast of injected polymer are seen in the main trunk (FIG. 6B). FIG. 6C shows the angiogram performed 14 days after the embolization of the renal artery. Note the main trunk (paired arrowheads) remained completely occluded. Distal occlusion of the left adrenal artery (long arrow), which is originated at the proximal segment of the renal artery, was also seen.

Histologic Evaluation of Treated Tissues

Figure 7:
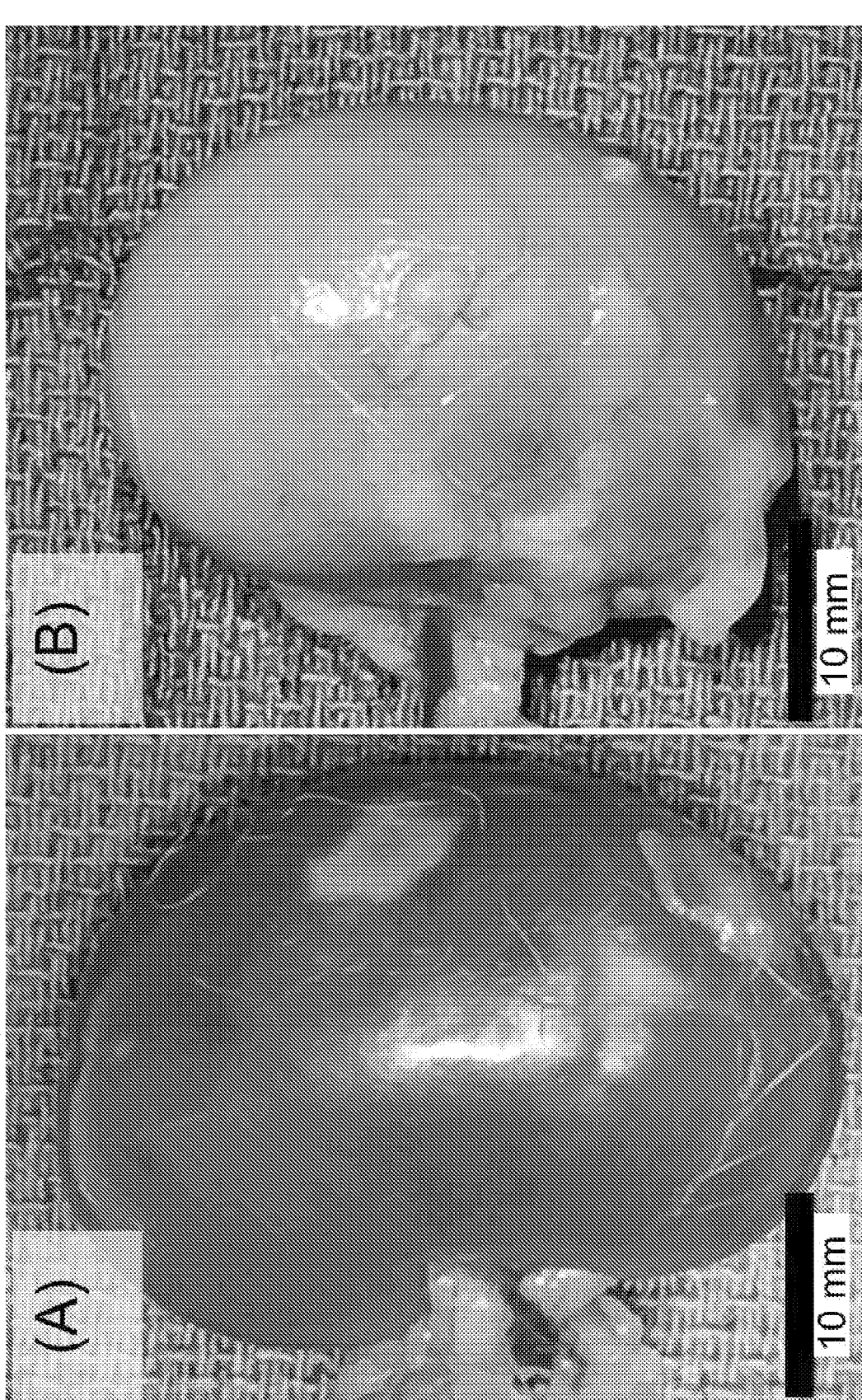
FIG. 7 is a digital photograph providing a macroscopic view of the harvested kidney tissues 14 days after treatment. Panel (A) shows the right kidney (untreated) as a control organ. The extracted kidney as well as artery/vein complex at the hilum show homogenous reddish color and a smooth surface. Panel (B) shows the left kidney embolized with GBLEM after 14 days. Discoloration and reduced size of the organ were confirmed. Scale bar is 10 mm.

The animal was then sacrificed to perform histologic evaluation of the treated artery and kidney. The harvested kidney tissue was macroscopically compared with the other side, which was used as a control (FIG. 7A). The kidney samples occluded with GBLEM showed remarkably reduced size and yellowish discoloration indicating the tissue atrophy induced by the absence of blood supply (FIG. 7B). The microscopic analysis is now under investigation. The results above showed that the treated artery remained completely occluded for 14 days after the implantation, indicating the persistent and durable mechanical property of the GBLEM.

(b) Angiographic Evaluation Using *Rete mirabile* of Swine

Experiment #3, Animal: Yorkshire swine, female
Weight: 35 kg
GBLEM used: gellan gum, 1.34 wt %; D-glucose, 9.0 wt %; [I]=140 mg/mL (iohexol)

Endovascular Procedures

Under general anesthesia, right femoral artery was punctured with 4F micropuncture kit, and 6F sheath was placed. With the iv drip of the heparinized saline from the left ear vein, the procedure was started. A 6F guiding catheter was placed in the left ascending pharyngeal artery, and digital subtraction angiography (DSA) was performed. Due to the concern about the occlusion of the vessel by the mechanical stimulation of the guiding catheter, 50 μg of nitroglycerin was injected into the vessel via the guiding catheter.

Angiographical Results

A microcatheter (Echelon 10) was advanced via the guiding catheter and placed in the left ascending pharyngeal artery near the *Rete mirabile* (bAVM model) and flushed with heparinized saline. Next, the GBLEM was loaded into a 1 mL syringe, and the syringe was connected to the microcatheter. The GBLEM was slowly injected into the bAVM model under the DSA monitoring. After observation of the distal migration of the GBLEM into the left internal carotid artery (ICA), the injection was held for 10-15 seconds and resumed again. Finally, a total volume of 0.9 mL was injected into the vessel over approximately 5 min, until a sufficient occlusion of the bAVM followed by the reflux into the parent vessel were confirmed.

The visibility was fair to observe the movement of the injected material. The behavior of the material was similar to that of Onyx embolic material. The distal migration after deployment of the GBLEM was observed, which indicated that the target vessel was not densely occluded at the beginning, due to the suboptimal occlusion speed. Therefore, injection speed was reduced during the second injection and relatively long injection was performed. Once the occlusion of the bAVM model was seen, a reflux into the ascending pharyngeal artery (APA) was observed. At the same time, it was seen that the material in the vessel was gradually being pushed into the bAVM model. Therefore, an additional injection of the material was performed to confirm a stable and complete occlusion of the vessel. Finally the microcatheter was completely withdrawn. No catheter entrapment occurred.

Experiment #4, Yorkshire swine, female
Weight 40 kg
GBLEM used: gellan gum, 1.34 wt %; D-glucose, 9.0 wt %; [I]=230 mg/mL (iohexol)

Endovascular Procedures

Under general anesthesia, femoral access was made using micropuncture kit followed by insertion of a 6F short sheath. A 6F guiding catheter was placed in the left common carotid artery, and control injection was performed. Next, the ascending pharyngeal artery was selected using microcatheter (Echelon 14) with Traxcess 014 microwire, and a super-selective injection was performed to visualize the *Rete mirabile* (bAVM model).

Results on Injection

Figure 8:
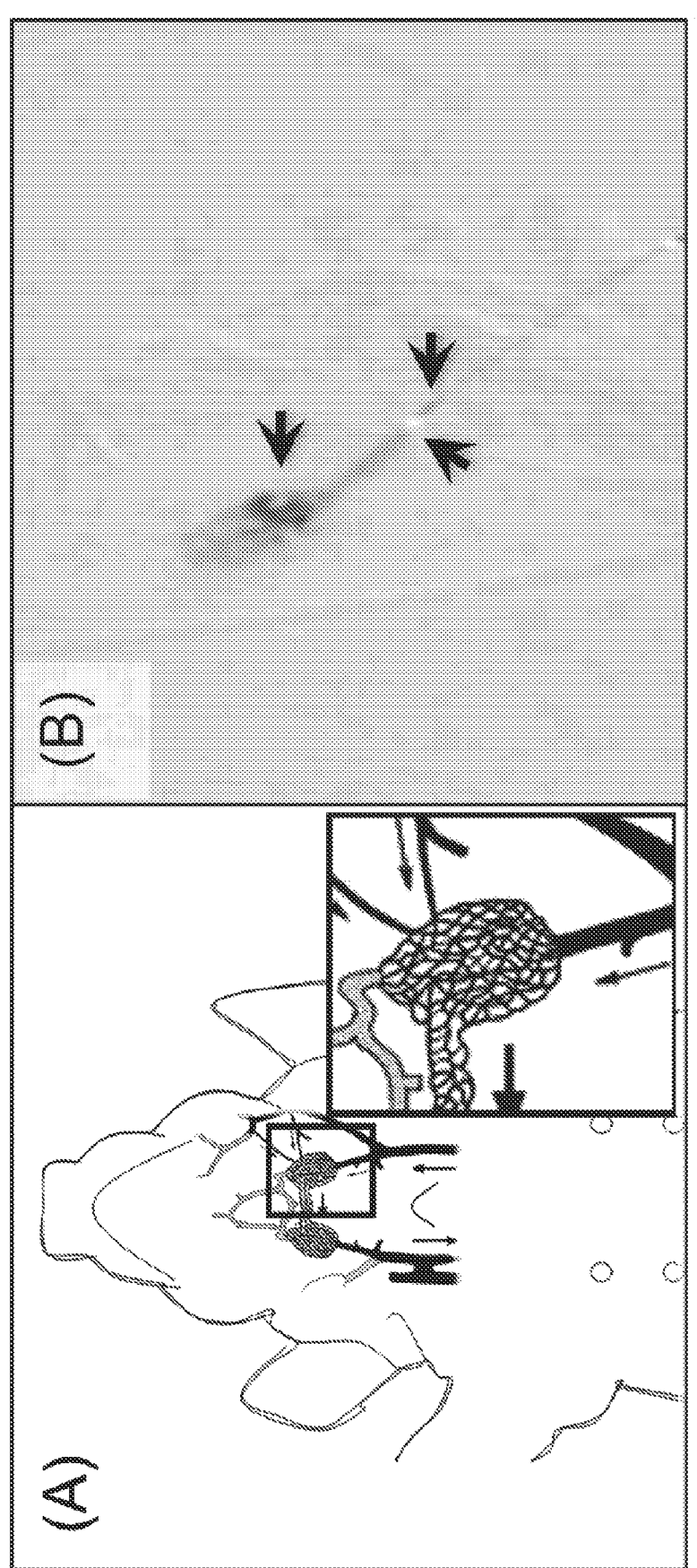
FIG. 8 illustrates an evaluation of gellan-based liquid embolic material (GBLEM) using the swine AVM model. Panel (A) is an illustration of the swine *Rete mirabile* (RM) as brain AVM model vessels. Inset shows a magnified view of boxed area in the left RM. Panel (B) shows GBLEM injected under digital subtraction angiography (DSA) showing injection of GBLEM. Complete occlusion of the bAVM model is confirmed after GBLEM was delivered to the bAVM model vessels (swine RM), as noted at top-most arrow. The lower left arrow points to the tip of the microcatheter. The lower right arrow points to the proximal reflux of GBLEM after filling the RM.

The GBLEM material (0.8 mL in total) was slowly injected into the bAVM model until the reflux of the material was observed (FIG. 8). No distal migration to the internal carotid artery (ICA) was observed. Once the reflux was seen, injection was held for 5-10 seconds, and resumed again. After several injections of the GBLEM, the proximal segment of the parent artery was completely filled, and then the injection was stopped.

The visibility for the [I]=230 mg/mL preparation was much better than that of the GBLEM with [I]=140 mg/mL, and the movement of the injected material with [I]=230 mg/mL was clearly visualized. There was no sign of recanalization or the material pushed into the distal vessels. Overall the GBLEM exhibited the better performance as compared to the alginate-based LEM of the prior art [WO2019163012].

Experiment #5, Yorkshire swine, female
Weight: 40 kg
GBLEM used: gellan gum, 1.34 wt %; D-glucose, 9.0 wt %; Angiographic contrast, tantalum (Ta) powder, 12 wt %

Results on Injection

The GBLEM (0.8 mL) with tantalum powder 12 wt % (no iohexol) was slowly injected into the bAVM model (right side) until the reflux of the material was observed. No distal migration to the ICA was observed. Once the reflux to the microcatheter was observed, injection was stopped, and resumed in 5-10 seconds. After several injections of the material, the proximal segment was completely filled, and the injection was stopped.

The visibility of Ta powder was better than that of the GBLEM with [1]=140 mg/mL and similar to that of the [I]=230 mg/mL preparation. The movement of the injected material was clearly observable with the radiopaque contrast of Ta particles. There was no sign of recanalization or the distal migration of the injected materials.

CONCLUSION

GBLEM is a novel liquid embolic material utilizing the mechanism of BCTC principle. That is to say the material is an injectable liquid, which is immediately activated and solidified upon contact with $Ca^{2+}$ ions in blood plasma. The main composition of the GBLEM, which is gellan gum, has a long history of commercial use in the food industry with excellent biological inertness. The gellan gum, a high molecular weight polysaccharide, was selected as the active ingredient by the present inventors, who found how to use gellan gum at higher concentration as compared to that in the prior art alginate-based LEM [WO2019163012]. In the present invention, the new discovery included the use of polyols/amino acids as the pre-injection gelling suppressor, with which much more durable and solid embolization becomes possible with much higher concentration of gellan gum without losing the fluidity of the material before the injection from the small-profiled microcatheters preferably used for neuroendovascular therapies. This also suggests that the application scope of GBLEM can be potentially expanded to the body endovascular ones, in which larger-profiled catheters are often selected.

A series of the preliminary data obtained from the in vivo experiments using renal arteries in rabbit and *Rete mirabile* (bAVM model) in swine indicated that the GBLEM was superior as compared to the prior art alginate based LEM. Embolization performance of the GBLEM showed promising results in which immediate coagulation occurred upon contact with blood flow with minimal volume of the material used (less than 1 mL).

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A composition comprising:
   (a) 0.8-2.0 wt % gellan gum;
   (b) 0.01-20 wt % low molecular weight polyols and/or amino acids, wherein the low molecular weight polyols have a molecular mass less than 1000 Daltons; and
   (c) 10-40 wt % radiopaque material.

2. The composition of claim 1, wherein the gellan gum of (a) is 0.8-1.0 wt %.

3. The composition of claim 1, wherein the low molecular weight polyols and/or amino acids of (b) is 3-10 wt %.

4. The composition of claim 1, wherein the composition retains a sol state upon annealing to 30-40° C.

5. The composition of claim 1, which is free of alginate.

6. The composition of claim 1, further comprising alginate.

7. The composition of claim 1, wherein the low molecular weight polyols are selected from the group consisting of: glucose, mannose, glucitol, mannitol, ribose, arabinose, and xylose.

8. The composition of claim 1, wherein the low molecular weight amino acids are selected from the group consisting of: glycine, alanine, valine, leucine, β-alanine, sarcosine, glutamate, aspartate, pyroglutamate, proline, serine, betaine, hydroxyproline, and threonine.

9. A method of preparing a liquid embolic composition, the method comprising combining, at 80-90° C.:
   (a) 0.8-2.0 wt % gellan gum solution,
   (b) 0.01-20 wt % low molecular weight polyols and/or amino acids; and
   (c) 10-40 wt % radiopaque material,
   wherein the low molecular weight polyols have a molecular mass less than 1000 Daltons.

10. The method of claim 9, wherein the gellan gum of (a) is 0.8-1.0 wt %.

11. The method of claim 9, wherein the low molecular weight polyols and/or amino acids of (b) is 3-10 wt %.

12. A method of embolizing a target blood vessel in a subject, the method comprising:
    (a) introducing a catheter into the target blood vessel; and
    (b) injecting a composition of claim 1 into the target blood vessel via the catheter.

13. The method of claim 12, wherein step (b) is performed under fluoroscopy.

14. The method of claim 12, wherein step (b) is performed until complete occlusion of the target blood vessel is confirmed.

15. The method of claim 12, wherein the target blood vessel is a cerebral artery.

16. A composition consisting of:
    (a) 0.8-2.0 wt % gellan gum;
    (b) 0.01-20 wt % low molecular weight polyols and/or amino acids; and
    (c) 10-40 wt % radiopaque material,
    wherein the low molecular weight polyols have a molecular mass less than 1000 Daltons.

* * * * *